United States Patent [19]

Ryder et al.

[11] Patent Number: 4,659,911

[45] Date of Patent: Apr. 21, 1987

[54] PLUG-IN CONTACT LENS DISINFECTOR WITH BIMETALLIC TIMER

[75] Inventors: Francis E. Ryder, Arab; Rowland W. Kanner, Guntersville, both of Ala.

[73] Assignee: Ryder International Corporation, Arab, Ala.

[21] Appl. No.: 734,410

[22] Filed: May 14, 1985

[51] Int. Cl.[4] ............................................. H05B 3/06
[52] U.S. Cl. .................................... 219/521; 219/439; 219/492; 219/505; 219/510; 219/541; 422/117
[58] Field of Search .............. 219/521, 541, 386, 439, 219/510, 512, 491, 492, 504, 505; 422/117, 38, 307

[56] References Cited

U.S. PATENT DOCUMENTS

| | | | |
|---|---|---|---|
| 3,031,565 | 4/1962 | Appleton et al. | 219/510 X |
| 3,064,102 | 11/1962 | Cassidy | 219/510 X |
| 3,083,283 | 3/1963 | Levinn | 219/510 X |
| 3,201,566 | 8/1965 | Schreyer | 219/510 X |
| 3,998,590 | 12/1976 | Glorieux | 21/89 |
| 4,158,126 | 6/1979 | Seitz | 219/439 |
| 4,178,499 | 12/1979 | Bowen | 219/439 |
| 4,270,039 | 5/1985 | Hauser | 219/439 |
| 4,341,948 | 7/1982 | Sundstrom et al. | 219/521 |
| 4,388,521 | 6/1983 | Thomas et al. | 219/521 |
| 4,529,868 | 7/1985 | Bowen et al. | 219/521 |

Primary Examiner—C. L. Albritton
Attorney, Agent, or Firm—Trexler, Bushnell, Giangiorgi & Blackstone, Ltd.

[57] ABSTRACT

There is disclosed a modular contact lens disinfecting system comprising a combination carrying case-and-heater module including a pair of receptacles for receiving a pair of contact lenses therein, a heating arrangement responsive to a predetermined electrical current for producing heat and positioned and configured for radiating heat to the receptacle, and electrical connectors coupled with the heating arrangement for receiving electrical current; and an energizing-and-timer module including a housing, an AC plug coupled with the housing for coupling an AC receptacle to receive electrical current, mating electrical connectors coupled to the housing for complementary mating with the electrical connectors of the case-and-heater module, and a timer coupled in electrical circuit intermediate the plug and the mating electrical connectors for controlling the time duration during which electrical current is applied to the mating electrical connectors. A novel timer structure is also provided comprising an elongate heat transfer element having a predetermined rate of heat transfer longitudinally thereof; a heating sleeve in engagement with one end portion of the heat transfer element; a heat responsive element in engagement with an opposite end of the heat transfer element; a switch having open and closing circuit positions for respectively opening and closing an electrical circuit to the heating sleeve; the heat responsive means being responsive to a predetermined amount of heat energy for actuating the switch to its open circuit position.

28 Claims, 9 Drawing Figures

PLUG-IN CONTACT LENS DISINFECTOR WITH BIMETALLIC TIMER

BACKGROUND OF THE INVENTION

This invention is directed generally to the field of contact lens disinfecting systems and more particularly to a novel and improved modular contact lens disinfecting system including a novel combination lens case and heater module and a novel combination energizing-and-timer module.

In recent years, soft and extended wear type of contact lenses have been developed as an alternative to the hard contact lenses. These soft and extended wear contact lenses are manufactured of a hydrophilic plastic porous material which can be formed to the desired lens curvature, and thereafter will absorb water and become relatively soft and pliable.

While hard contact lenses require periodic cleaning and disinfecting, the disinfecting of the soft and extended wear contact lenses is recommended more frequently. In this regard, the disinfecting of the soft lenses is recommended on a daily basis, whereas extended wear lenses as the name denotes, may be worn for a more extended period of several days, but should likewise be disinfected intermediate such periods of wear. This need for disinfecting is largely due to the porous nature of the plastic materials utilized in the construction of these newer types of lenses. Such porous material receives bodily fluids during wear which may have a number of materials dissolved therein. These dissolved materials may precipitate out and build up over time in the pores and this results in a clouding of the lens. Thorough cleaning is therefore necessary from time to time to remove this material from the pores. Moreover, such pores provide areas for bacterial growth and hence the lenses must be disinfected periodically.

Several disinfecting methods have been developed and employed with success in conjunction with soft and extended wear lenses. One such method involves placing the lenses in a saline or other disinfecting solution and thereafter heating the solution to a temperature sufficient to destroy any bacteria which may be present. A second method utilizes a chemical process to destroy the bacteria.

The thermal or heat disinfecting methods may employ either a "wet heat" process or a "dry heat" process. In the former process, the lenses are placed in a case containing a quantity of disinfecting or saline solution and the case is then placed in a second vessel containing a quantity of water which is brought to a boil, with heat being transferred to the lenses and solution in the case by way of the surrounding water. On the other hand, in the latter dry heat method of sterilization, the lenses are placed in the lens case with a quantity of disinfecting solution; however, the case is then placed in surface-to-surface contact with a heater unit. Hence, direct application of heat is obtained from the heater unit to the lens case and thence to the solution contained therein.

The present invention pertains to a disinfecting unit and system adapted for use in the "dry heat" type of process. In this regard, the present invention advantageously provides a novel modular disinfecting system design which utilizes a pair of relatively compact and easy to use modules. The first module comprises a combined case-and-heater unit module and may be utilized as a carrying case for the lenses intermediate periods of wear and/or disinfecting operations. The second unit comprises a combined energizing-and-timer unit which may be coupled with a conventional electrical outlet to receive electrical current. The two modules include mating sets of contacts for delivering energizing current from the energizing-and-timer module to the heater portion of the case and heater unit; and the timer portion of the energizing-and-timer module controls the amount of time during which this current is supplied thereby.

OBJECTS AND SUMMARY OF THE INVENTION

Accordingly, it is a general object of the invention to provide a novel and improved contact lens disinfecting system.

A more particular object is to provide a system in accordance with the foregoing object which employs a novel modular design wherein both a lens and a heating arrangement is provided in a first module and an electrical energizing circuit and timer is provided in a second module.

A related object is to provide a novel and improved timer design for use in conjunction with a system in accordance with the foregoing objects.

Briefly, and in accordance with the foregoing objects, a modular contact lens disinfecting system comprises a combination carrying case-and-heater module including a pair of receptacles for receiving a pair of contact lenses therein, heater means responsive to a predetermined electrical current for producing heat, said heater means being configured and positioned in said module for radiating heat to said receptacle for disinfecting contact lenses therein, and electrical connector means coupled with said heater means for receiving said predetermined electrical current; and an energizing-and-timer module including a housing, AC plug means coupled with said housing for coupling with an AC receptacle to receive said predetermined electrical current, mating electrical connector means coupled to said housing for complementary mating with the electrical connector means of said case-and-heater module, and timer means coupled in electrical circuit intermediate said plug means and said mating electrical connector means for controlling the time duration during which said predetermined electrical current is applied to said mating electrical connector means.

In accordance with a further aspect of the invention a novel timer structure is also provided for the energizing and timer module comprising elongate heat transfer means having a predetermined rate of heat transfer longitudinally thereof; heating sleeve means in thermal contact with a source of heat and with one end portion of said elongate heat transfer means; heat responsive means in engagement with an opposite end of said heat transfer means; switching means having open and closed circuit positions for respectively opening and closing an electrical circuit for energizing said source of heat said heat responsive means being responsive to a predetermined amount of heat energy for actuating said switching means to its open circuit position.

BRIEF DESCRIPTION OF THE DRAWINGS

The features of the present invention which are believed to be novel are set forth with particularity in the appended claims. The organization and manner of operation of the invention, together with further objects and advantages thereof, may best be understood by reference to the following description taken in connection with the accompanying drawings, in the several figures of which like reference numerals identify like elements, and in which:

DETAILED DESCRIPTION OF THE ILLUSTRATED EMBODIMENT

Figure 1:
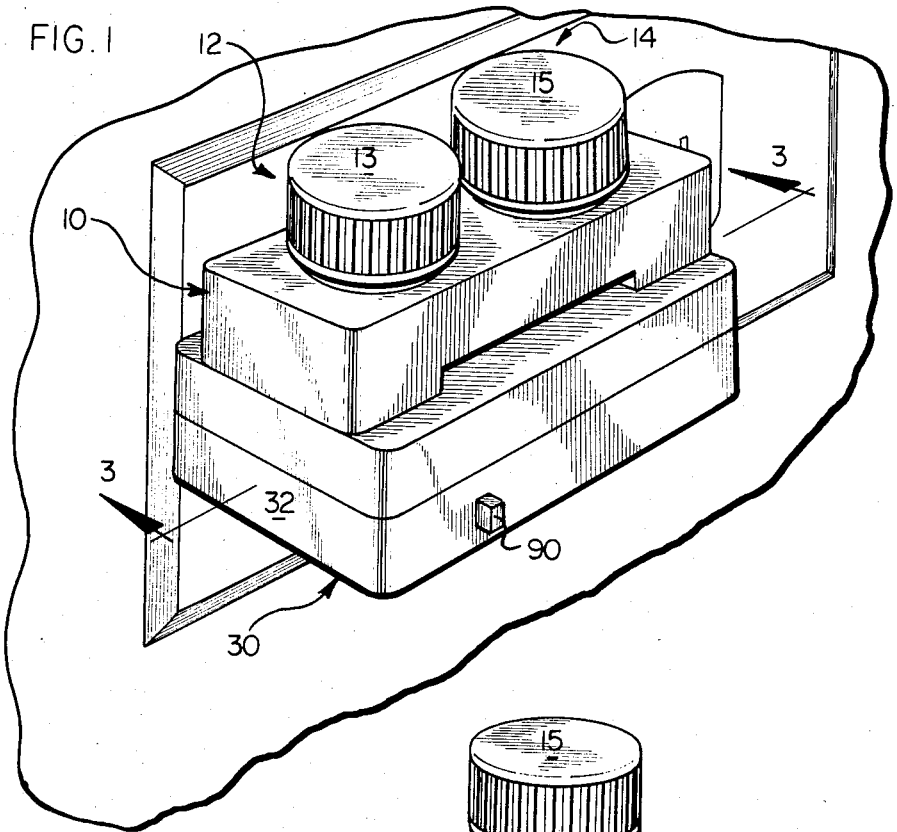
FIG. 1 is a perspective view illustrating the modular contact lens disinfecting system of the present invention in use for disinfecting contact lenses.
Figure 2:
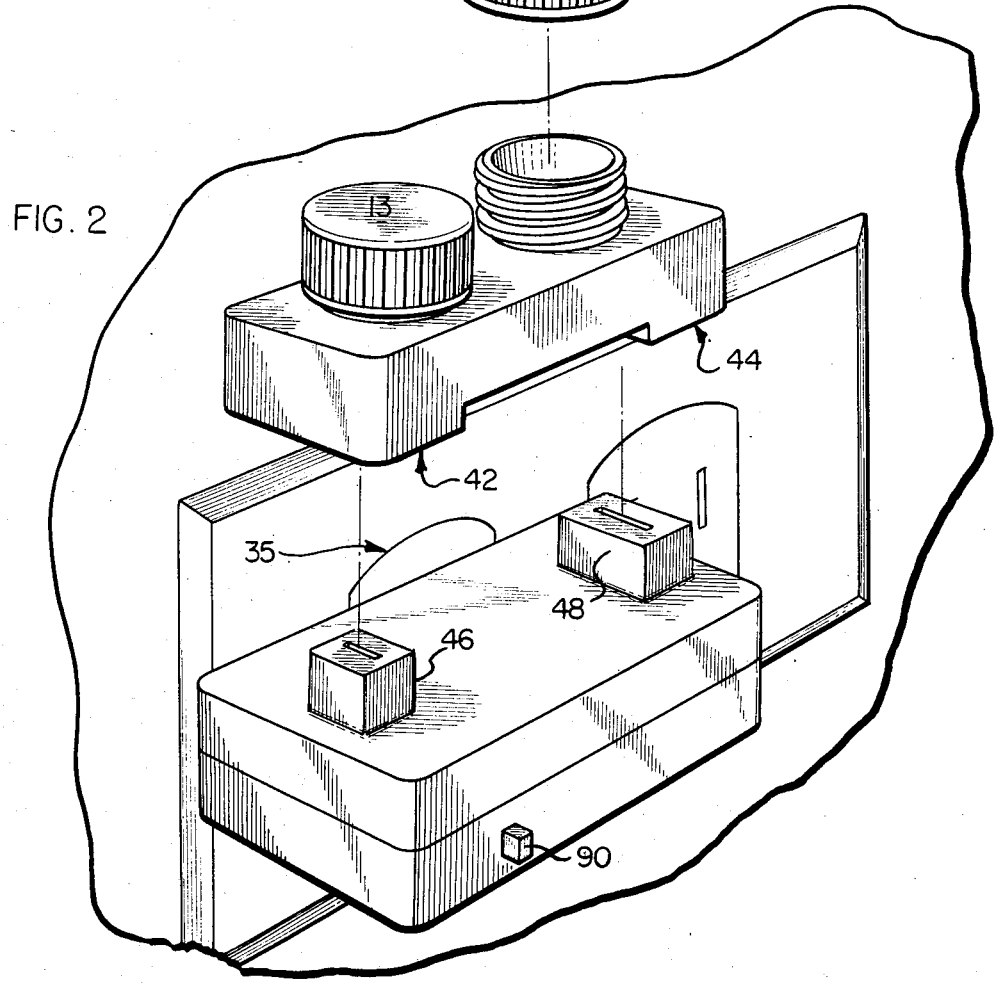
FIG. 2 is an exploded perspective view, similar to FIG. 1, illustrating further details thereof.

Referring now to the drawings and initially to FIGS. 1 and 2, a modular contact lens disinfecting system comprises a first, combination carrying case-and-heater module 10 which includes a base section 11 having a pair of receptacles designated generally 12 and 14, for receiving a quantity of disinfecting or saline solution and the contact lenses, formed therein. In this regard, removable covers 13 and 15 are provided for the receptacles 12 and 14, and preferably are threadably engageable therewith as illustrated in FIG. 2. Referring now to the upper portion of FIG. 3, the module 10 is shown in section. In this regard, it can be seen that this first module 10 also includes heater means designated generally by reference numeral 16. In the illustrated embodiment, the heater means 16 comprises a heating element 18 and a pair of electrically and thermally conductive members 20 and 22 which extend beneath the respective receptacles 12 and 14 for transfering heat energy from the heating element 18 to these receptacles. Hence, the heater means is configured and positioned in the first module for radiating heat to the receptacles for the purpose of disinfecting contact lenses placed therein.

The conductive members 20 and 22 are also formed to define electrical connector means 24 and 26, which are therefore electrically coupled with the heater means. These connector means are arranged to extend outwardly of module 10 to receive a predetermined electric current to thereby effect heating of the heater means, including both the element 18 and members 20 and 22. In this regard, the heating element 18 is responsive to a predetermined electrical current for producing heat. This heat is then conducted readily by members 20 and 22.

A second, energizing-and-timer module is designated generally by reference numeral 30. This second module 30 includes a housing 32 and an AC plug or plug means 34 (see FIG. 7) coupled with the housing 32 for coupling with an AC receptacle 35 to receive the predetermined electrical current for energizing the heater means 16. The second module also includes electrical connector means or receptacle means 36 and 38 for mating with the electrical connector means 24 and 26 of the first module. Timer means designated generally by the reference numeral 40 are coupled in electrical circuit intermediate the plug 34 and the mating electrical connectors 36 and 38 for controlling the time duration during which the predetermined electrical current is applied to these mating electrical connectors 36 and 38.

Figure 3:
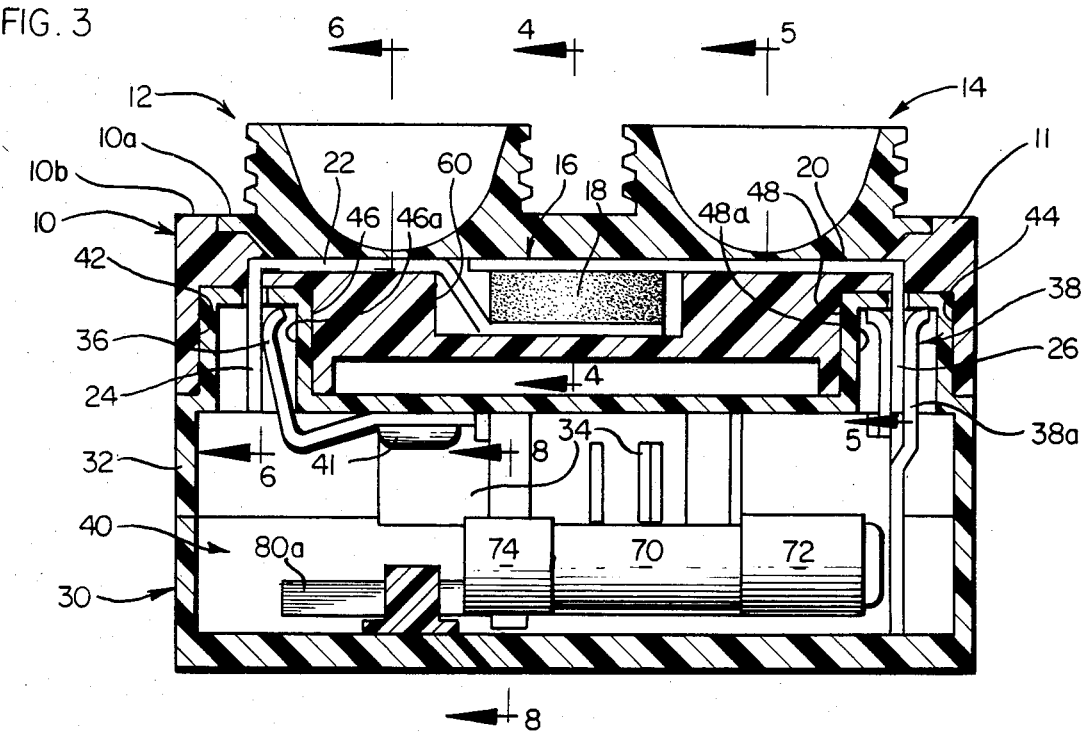
FIG. 3 is an enlarged sectional view taken generally in the plane of the line 3—3 of FIG. 1.

Accordingly, when the first or case-and-heater module is coupled with the second or energizing-and-timer module as illustrated in FIGS. 1 and 3 for example, electrical current is applied by way of the timer means 40 and respective mated electrical connectors 36, 24 and 38, 26 to the heater means 16 comprising the heating element 18 and thermal conductor members 20 and 22. Advantageously, the foregoing arrangement permits control of the time duration of application of heat to contact lenses received in receptacle 12 and 14 to thereby provide a controlled, dry heat disinfecting system.

Referring now to FIGS. 1 through 6, it will be seen that complementary mating mechanical coupling means 42, 44 and 46, 48 are formed or defined respectively on the case-and-heater module and on the energizing-and-timing module for releasably coupling the modules together with the respective electrical connectors 24, 26 and 36, 38 thereof in electrically conductive contact. As best seen in FIG. 3, the electrical connector means of the case-and-heater module comprises male connector portions 24 and 26 which form extensions of the previously mentioned thermally and electrically conductive plate members 20 and 22. The mechanical coupling means 42 and 44 comprise a female coupling portion located in surrounding relation to these electrical connectors 24 and 26. Cooperatively, the mating electrical connector 38 of the energizing-and-timer module comprises a female connector portion defined by a pair of closely spaced relatively flat conductor members 38a and 38b for resiliently engaging connector 26 therebetween. The mechanical coupling means 46 and 48 comprise male coupling portions having respective recesses 46a and 48 therein for receiving the respective connectors 36 and 38. In this regard, the connector 36 comprises a relatively flat metallic conductive element which is formed for resiliently positively engaging connector 24, as best viewed in FIG. 3. As best viewed in FIG. 7, the conductive members 38a and 38b making up connector 38a are coupled together at a lower portion thereof, as with a rivet 39. A similar rivet 41 secures connector 36 to housing 32. Moreover, it will be seen that connector 36 and one prong 34a of AC plug 34 are formed as a unit in the illustrated embodiment.

Referring now more particularly to the heating means 16, it will be seen that the case-and-heater module 10 defines an interior compartment 60 into which the heating element 18 is disposed. In the illustrated embodiment, this heating element 18 comprises a combination heater-and-thermostat element, and preferably a positive temperature coefficient (PTC) thermistor. Such PTC thermistor elements are well known in the art and are available for example from Keystone Carbon Company Thermistor Division, St. Marys, Pa. 15857.

Figure 4:
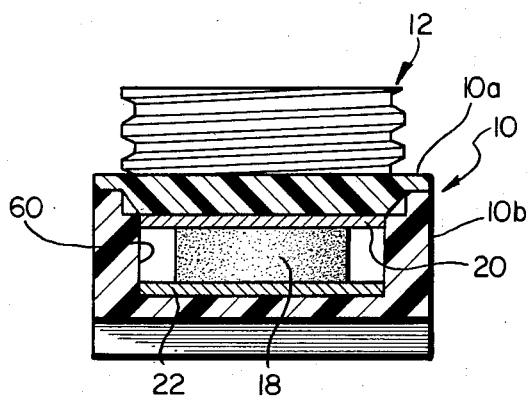
FIG. 4 is a partial sectional view taken generally in the plane of the line 4—4 of FIG. 3.
Figure 5:
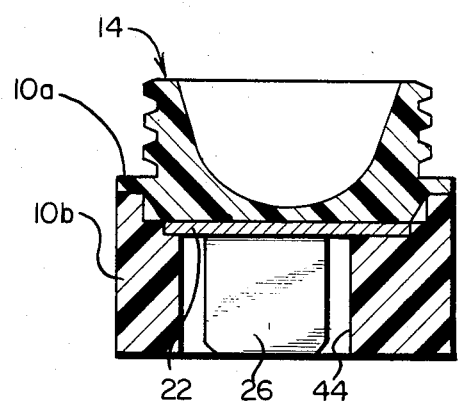
FIG. 5 is a partial developmental view taken generally along the line 5—5 of FIG. 3.
Figure 6:
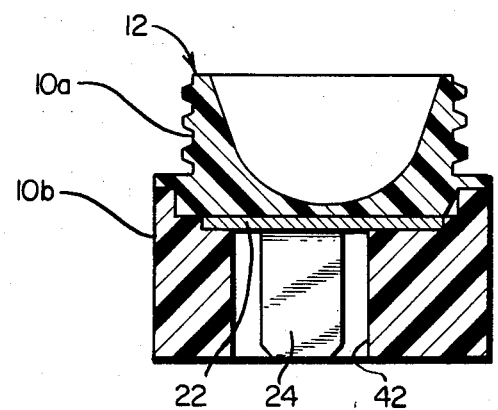
FIG. 6 is a developmental view taken generally along the line 6—6 of FIG. 3.

As previously mentioned, both electrical and thermal conduction to and from the heater element 18 are accomplished by plate-like electrically and thermally conductive members 20 and 22. These members underly the respective lens receptacles and are in both electrical and thermal engagement with the heater-and-thermostat element 18. As previously indicated, the connector means of the case-and-heater module comprise projecting end parts 24 and 26 of the plate-like conductive members 20 and 24. Further details of the foregoing connector structures are illustrated in FIGS. 4 through 6, to which reference is also invited. In the illustrated embodiment, it will be seen that the receptacles 12 and 14 are integrally formed in a first member or portion 10a of the module 10 and this member is non-removably affixed to a second or base member or portion 10b to form the module 10. The above-mentioned recess 60 for receiving the heating element 18 is formed in the latter member or portion 10b, and enclosed or covered by the former member 10a.

Figure 7:
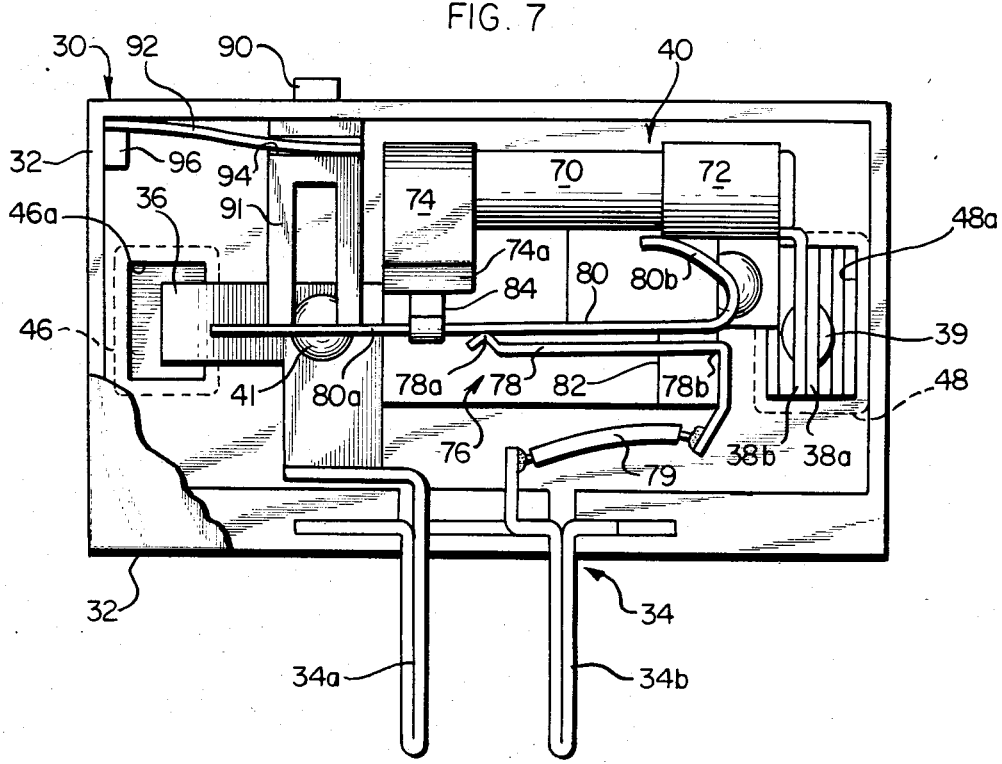
FIG. 7 is a top plan view, partially broken away, showing an energizing-and-timer module of the invention.
Figure 8:
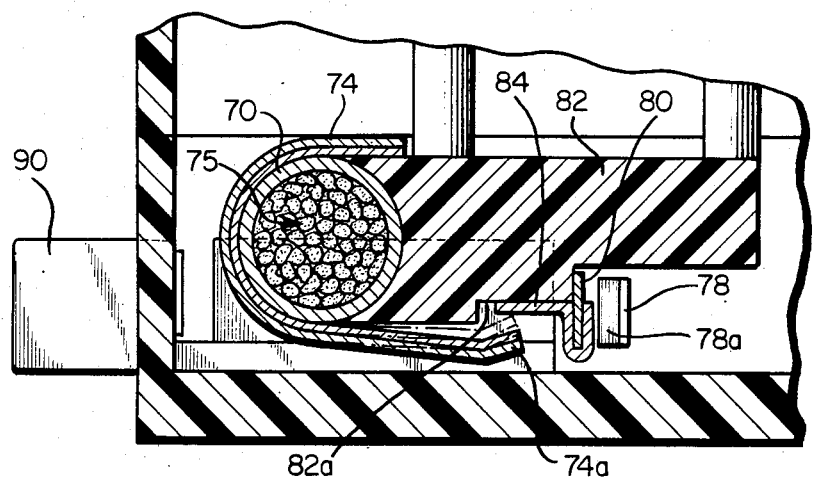
FIG. 8 is an enlarged partial sectional view taken in the plane of the line 8—8 of FIG. 3.
Figure 9:
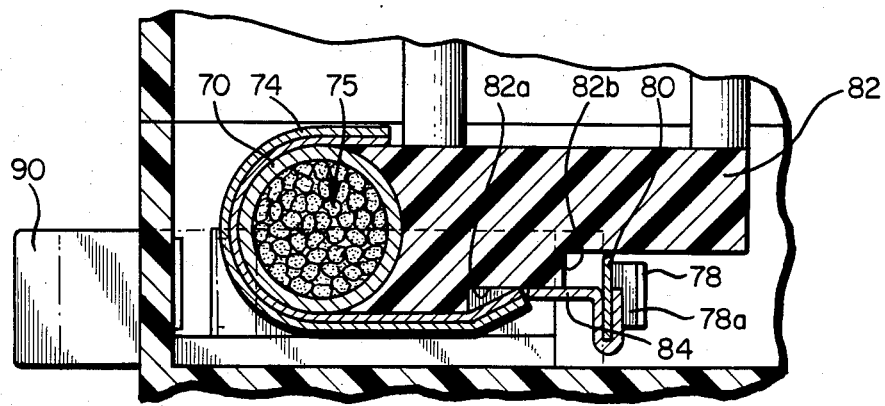
FIG. 9 is a partial sectional view similar to FIG. 8 and illustrating a moved position of elements thereof.

Referring now to FIGS. 7, 8 and 9 the timer means 40 is illustrated and will next be described in detail. More specifically, the timer means 40 includes an elongate heat transfer element or means 70 which in the illustrated embodiment comprises an elongate tubular member of predetermined dimensions filled with a preselected meltable material. Preferably, this meltable material has a predetermined melting rate in response to heat energy applied thereto, and may comprise, for example, a wax or paraffin or wax-like material. A heating sleeve means 72 is mounted in surrounding engagement with one end portion of the elongate tubular member 70 and a second heat responsive means or sleeve 74 is mounted in surrounding engagement with an opposite end of the tubular member 70.

A switch or switching means 76 is provided in circuit with the plug 34, and connectors 36 and 38, said switch 76 being disposed intermediate prongs 34a and 34b, and also intermediate connectors 36 and 38. The switch means 76 has open circuit and closed circuit positions for respectively opening and closing an electrical circuit through the module 30 from the AC plug 34 to the electrical connectors 36, 38. With the switch or switching means 76 in the closed circuit condition, energizing electrical current will be fed to the conductors 36, 38 and hence to heater means 16, when the modules 10 and 30 are coupled together as in FIG. 1. Accordingly, heat energy will be transferred from heater 18 by way of conductive members 20 to connector 38. It will be noted that conductor 38b of connector 38 is preferably formed integrally with sleve 72. Hence, heat energy is also conducted to sleeve 72 and thence to the tubular member or heat transfer means 70. Upon expiration of a predetermined or measurable interval of time, the heat transfer member, by way of the meltable material therein, will transmit sufficient heat energy to heat responsive means 74 to cause actuation of the switch 76 to its open circuit position. This will then remove energizing current from heating element 18 and therefore cease the application of heat to sleeve 72, heat transfer member 70 and heat responsive means 74. From the foregoing it will be appreciated that the sleeve 72 is in both electrical and thermal connection with connector member 38 band therefore with the heating element 18 of the first module 10, this thermal connection and electrical circuit being completed by way of connectors 26 and 36.

Referring now also to FIGS. 8 and 9, the heat responsive means or sleeve 74 comprises a generally U-shaped bimetallic element in surrouding relation with substantially one-half of an end portion of tubular member 70 opposite its end surrounded by sleeve 72. The meltable material is indicated generally by reference numeral 75. The switching means or switch 76 will be seen to comprise a pair of flat, elongate, metallic, spring-like elements formed to define switch leaves 78 and 80.

Switch leaf 78 will be seen to be coupled by a wire 79 to one prong 34b of the AC plug member 34, and to include a contact portion 78a which projects generally in the direction of second switch leaf 80. This switch leaf 78 is mounted at one end thereof in a mounting member or block 82, and bent or formed at 78b to thereby define a spring-like resilience to the outer end thereof in which contact portion 78a is formed.

Second switch leaf 80 is also mounted to mounting block or member 82 to define resiliently deformable spring-like movement of an outwardly extended end 80a thereof. At a region about midway toward this end 80a, leaf 80 mounts a flat, spade-like member or ear 84 which is slideable along a surface 82 of a block 82 for engagement with bimetallic element 74 in a manner which will be described shortly. An opposite end of leaf 80 is bent into a generally U-shaped configuration as indicated generally at 80b for positive electrically conductive contact with sleeve 72.

The mounting of leaf 80 with respect to leaf 78 is such that outer end 80a is normally biased in a direction away from contact with contactor portion 78a. However, as viewed in FIGS. 7 and 9, an outwardly extending portion 74a of bimettallic member 74 normally engages or abuts an end surface of the projecting spade-like member or ear 84, to normally hold switch leaf 80 in electrically conductive contact with contact portion 78a of leaf 78.

As best viewed in FIG. 8, upon transmission of sufficient heat energy thereto, bimetallic element 74 expands, thereby lifting outwardly extending portion 74a thereof above surface 82a of the mounting block 82. This permits the spring-like bias on extending portion 80a of leaf 80 to slide the outwardly projecting ear 84 along surface 82a and into the space between surface 82a and raised portion 74a of the expanded element 74, thus moving leaf 80 out of contact with leaf 78 and defining an open circuit position of switch 76.

In the illustrated embodiment, surface 82a will be seen to define a shoulder portion in mounting block 82. Also outwardly projecting end part 74a of bimetallic element 74 will be seen to be bent or otherwise formed somewhat in the direction of this surface 82a for normally engaging both surface 82a and an outer edge portion of projecting flat ear 84 as best viewed in FIG. 9. Moreover, a second similar shoulder portion of mounting block 82 forms an abutment or stop surface 82b for the leaf 80, defining the open circuit position of leaf 80 with respect to leaf 78, and particularly contact portion 78a thereof as best viewed in FIG. 8.

From the foregoing it will be appreciated that in operation, with switch 76 initially in the position illustrated in FIGS. 7 and 9, electrical energy will be supplied to the heating element 18 by way of sleeve 72 and connector 38. This of course assumes that the module 10 is engaged with the module 30 as illustrated in FIGS. 1 and 3. The heat energy provided by heating element 18 will be transferred to heating sleeve 72 by way of plate-like member 20 and its connector portion 26 and cooperating connector 38. This heat energy will in turn be transferred by sleeve 72 to the meltable material 75 within tubular member 70. The meltable material 75 is preferably in the form of wax, or some other well known wax-like product which in the solid state is a poor conductor of heat, but will absorb heat energy over a period of time in converting to the liquid state. Once in the liquid state, the material 75 will transmit heat along the length of the tubular member 70.

After a predetermined length of time, the material 75 in the tubular member 70 will melt, and upon sufficient melting will transfer transferring heat to bimetallic element 74. Upon receiving sufficient heat energy bimetallic element 74 will expand to the position shown in FIG. 8, thereby allowing spade-like ear 84 to slide along surface 82a, thereby placing switch 76 in an open circuit condition. With switch 76 in the open circuit condition, electrical current is no longer supplied to heating element 18, thus ending the disinfecting cycle for lenses in the receptacles 12, 14.

Moreover, heat energy is no longer supplied to the sleeve 72, tubular member 70 and material 75 therein, and bimetallic element 74. Accordingly, bimetallic element 74 will contract in response to a decrease in heat energy received thereby below said predetermined amount. Upon such contraction, end portion 74a will assume the position illustrated in phantom line in FIG. 8, engaging the flat ear member 84 against surface 82a and thus holding the switch 76 in the open circuit position.

The invention is claimed as follows:

1. A modular contact lens disinfecting system comprising: a first, combination carrying case-and-heater module comprising a pair of receptacles for receiving a pair of contact lenses therein, heater means responsive to a predetermined electrical current for producing heat, said heater means being configured and positioned in said first module for radiating heat to said receptacles for disinfecting contact lenses therein, and electrical connector means coupled with said heater means for receiving said predetermined electric current to thereby effect heating of said heater means; and an energizing-and-timer module including a housing, AC plug means coupled with said housing for coupling with an AC receptacle to receive said predetermined electrical current, mating electrical connector means for complementary mating with the electrical connector means of said case-and-heater module, and timer means coupled in electrical circuit intermediate said plug means and said mating electrical connector means for controlling the time duration during which said predetermined electrical current is applied to said mating electrical connector means.

2. A system according to claim 1 and further including complementary mating mechanical coupling means defined respectively on said case-and-heater module and on said energizing-and-timer module for releasably coupling said modules together with the respective electrical connectors thereof in electrically conductive contact.

3. A system according to claim 2 wherein the electrical connector means of said case-and-heater module comprises a male connector portion, and wherein the mechanical coupling means thereof comprises a female coupling portion in surrounding relation to said electrical connector means; wherein the mating electrical connector of said energizing-and-timer module comprises a female connector portion, and wherein the mechanical coupling means thereof comprises a male coupling portion dimensioned for interfitting with said female coupling portion and having a recess therein for receiving said electrical connector means.

4. A system according to claim 1 wherein said case-and-heater module includes an interior compartment and wherein said heater means comprises a combination heater-and-thermostat element mounted in said interior compartment.

5. A system according to claim 4 wherein said combination heater-and-thermostat element comprises a positive temperature coefficient thermistor.

6. A system according to claim 1 wherein said case-and-heater module further includes a pair of cover means for removably covering said contact lens receptacles therein.

7. A system according to claim 4 wherein said heater means further comprises a pair of plate-like electrically and thermally conductive members underlying the respective lens receptacles and in both electrical and thermal engagement with said heater-and-thermostat element.

8. A system according to claim 7 wherein said electrical connector means of said case-and-heater module comprises projecting end parts of each of said plate-like conductive members.

9. A system according to claim 8 wherein the electrical connector means of said case-and-heater module comprises a male connector portion and the mechanical coupling means thereof comprises a female coupling portion in surrounding relation to said electrical connector means; and wherein the mating electrical connector of said energizing-and-timer module comprises a female connector portion and the mechanical coupling means thereof comprises a male coupling portion dimensioned for interfitting with said female coupling portion and having a recess therein for receiving said electrical connector means.

10. A system according to claim 1 wherein said timer means comprises heat transfer means having a predetermined rate of heat transfer longitudinally thereof; heating sleeve means in thermal and electrical engagement with said mating electrical connector means and in thermal engagement with one end portion of said heat transfer means; heat responsive means in engagement with an opposite end of said heat transfer means; switching means having open circuit and closed circuit positions for respectively opening and closing an electrical circuit from said AC plug means to the mating electrical connector means said heat responsive means being responsive to a predetermined amount of heat energy received through said heat transfer means for actuating said switching means to its open circuit position.

11. A system according to claim 10 wherein said heat transfer means comprises an elongate tubular member of predetermined dimensions filled with a preselected meltable material, said meltable material having a predetermined melting rate in response to heat energy applied thereto.

12. A system according to claim 11 wherein said heating sleeve means comprises generally tubular sleeve means surroundingly engaging one end portion of said elongate tubular member.

13. A system according to claim 12 wherein said heat responsive means comprises a bimetallic element at least partially surroundingly engaged with an opposite end portion of said elongate tubular member and operatively engageable with said switching means.

14. A system according to claim 13 wherein said switching means includes a pair of switch leaves, one of said switch leaves being biased toward a position out of contact with the other of said switch leaves comprising the open circuit position; said bimetallic member being positioned for engaging said one switch leaf to hold it against said bias in a position in contact with the other switch leaf comprising the closed circuit position; said bimetallic element being responsive to said predetermined amount of heat energy for disengaging said open switch leaf for resilient return to the open circuit position for removing electrical current from the heating sleeve means.

15. A system according to claim 14 and further including a mounting member for mounting said switch leaves and said tubular member and having a first, substantially flat surface; wherein said one switch leaf includes a projecting, substantially flat ear portion slideable along a first surface of said mounting member; and wherein said bimetallic element includes a projecting end part normally engaged with said first surface and abutting said projecting ear to thereby hold said first switch leaf in said closed circuit position; said end part being spaced apart from said first surface by expansion of said bimetallic element in response to said predetermined amount of heat energy applied thereto, for allowing said projecting ear to slide between said end part and said first surface in response to said bias on said first switch leaf, to thereby assume the open circuit position; said bimetallic element thereafter contracting in response to a decrease in heat energy received thereby below said predetermined amount, and said end part pressing said projecting ear against said first surface to hold said first switch leaf in the open circuit position.

16. A system according to claim 15 and further including manual reset means for urging said first switch leaf in a direction for disengaging said ear from between said bimetallic element end portion and said first surface and returning said first switch leaf to the closed circuit position with said bimetallic element and portion abutting said projecting ear.

17. A combination energizing and timer module for use in a modular contact lens disinfecting system comprising: a housing, AC plug means coupled with said housing for coupling with an AC receptacle to receive electrical current; electrical connector means for complementary mating with electrical connector means of a further module to transfer electrical current thereto; and timer means coupled in electrical circuit intermediate said plug means and said electrical connector means for controlling the time duration during which said predetermined electrical current is applied to said electrical connector means; wherein said timer means comprises heat transfer means having a predetermined rate of heat transfer longitudinally thereof; heating sleeve means in electrical and thermal contact with said electrical connector means and in thermal engagement with one end of said heat transfer means; heat responsive means in engagement with an opposite end of said heat transfer means; switching means having open and closed circuit positions for respectively opening and closing an electrical circuit from said AC plug means to the electrical connector means; said heat responsive means being responsive to a predetermined amount of heat energy received through said heat transfer means for actuating said switching means to its open circuit position; and wherein said heat transfer means comprises an elongate tubular member of predetermined dimensions filled with a preselected meltable material, said meltable material having a predetermined melting rate in response to heat energy applied thereto.

18. A system according to claim 17 wherein said heating sleeve means comprises sleeve means surroundingly engaging one end portion of said elongate tubular member.

19. A system according to claim 18 wherein said heat responsive means comprises a bimetallic element surroundingly engaged with an opposite end portion of said elongate tubular member and operatively coupled with said switching means.

20. A system according to claim 19 wherein said switching means includes a pair of switch leaves, one of said switch leaves being biased toward the open circuit position comprising a position wherein it is out of contact with the other of said switch leaves; said bimetallic member being normally positioned for engaging said one switch leaf to hold it in the closed circuit position comprising a position wherein it is in contact with the other switch leaf, said bimetallic element being responsive to said predetermined amount of heat energy for disengaging said one switch leaf for resilient return to the open circuit position for removing electrical current from the heating sleeve means.

21. A system according to claim 20 and further including a mounting member for mounting said switch leaves and said tubular member and having a first, substantially flat surface; and wherein said one switch leaf includes a projecting substantially flat ear portion slideable along said first surface of said mounting member; wherein said bimetallic element includes an end part normally engaged with said first surface and abutting said projecting ear to thereby hold said one switch leaf in said closed circuit position; said end part being spaced apart from said first surface by expansion of said bimetallic element in response to a predetermined amount of heat energy applied thereto, for allowing said projecting ear to slide between said end part and said first surface in response to said bias on said one switch leaf, to thereby assume the open circuit position; said bimetallic element thereafter contracting in response to a decrease in heat energy received thereby below said predetermined amount, and said end part pressing said projecting ear against said first surface to hold said one switch leaf in the open circuit position.

22. A system according to claim 21 and further including manual reset means for urging said one switch leaf in a direction for disengaging said ear from between said bitmetallic element end portion and said first surface and returning said one switch leaf to the closed circuit position and with said bimetallic element end portion abutting said projecting ear.

23. A timer mechanism comprising: elongate heat transfer means having a predetermined rate of heat transfer longitudinally thereof; heating sleeve means in thermal contact with a source of heat and with one end of said heat transfer means; heat responsive means in engagement with an opposite end of said heat transfer means; switching means having open circuit and closed circuit positions for respectively opening and closing an electrical circuit for energizing said source of heat; said heat responsive means being responsive to a predetermined amount of heat energy received through said heat transfer means for actuating said switching means to its open circuit position; wherein said heat transfer means comprises an elongate tubular member of predetermined dimensions filled with a meltable material, said meltable material having a predetermined melting rate in response to the absorption of heat energy applied thereto.

24. A timer mechanism according to claim 23 wherein said heating sleeve means comprises sleeve means surroundingly engaging one end portion of said elongate tubular member.

25. A timer mechanism according to claim 24 wherein said heat responsive means comprises a bimetallic element surroundingly engaged with an opposite end portion of said elongated tubular member and operatively coupled with said switching means.

26. A timer mechanism according to claim 25 wherein said switching means includes a pair of switch leaves, one of said switch leaves being biased toward the open circuit position comprising a position wherein it is out of contact with the other of said switch leaves; said bimetallic member being normally positioned for engaging said one switch leaf to hold it in the closed circuit position comprising a position wherein it is in contact with the other switch leaf, said bimetallic element being responsive to said predetermined amount of heat energy for disengaging said one switch leaf for resilient return to the open circuit position for removing electrical current from the heating sleeve means.

27. A combination carrying case and heater member for contact lenses or the like, comprising: a base member; a pair of spaced receptacle means for the lenses formed in said base member; electrically energizable heat generating means disposed within said base member; a pair of thermally and electrically conductive members connected to said heat generating means for providing electrical current thereto, and said conductive members also being disposed proximate said receptacle means for conveying thermal energy from said heat generating means to said receptacle; wherein said conductive members extend from the base member for connection to a source of electrical power.

28. A combination carrying case and heater member according to claim 27 wherein said heat generating means is a thermistor device, said conductive members being relatively flat and each having a first portion in engagement with the thermistor device, on opposite sides thereof, respectively, and a second portion disposed proximate one of said receptacle means.

* * * * *